(12) United States Patent
O'Rear et al.

(10) Patent No.: US 6,768,037 B2
(45) Date of Patent: Jul. 27, 2004

(54) PROCESS TO UPGRADE FISCHER-TROPSCH PRODUCTS AND FORM LIGHT OLEFINS

(75) Inventors: Dennis J. O'Rear, Petaluma, CA (US); Stephen J. Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 15 days.

(21) Appl. No.: 10/283,759

(22) Filed: Oct. 30, 2002

(65) Prior Publication Data

US 2004/0087824 A1 May 6, 2004

(51) Int. Cl.$^7$ .............................. C07C 4/06; C07C 1/207
(52) U.S. Cl. ...................... 585/651; 585/653; 585/640; 585/639; 585/638
(58) Field of Search .............................. 585/651, 653, 585/640, 639, 638

(56) References Cited

U.S. PATENT DOCUMENTS

| | | | |
|---|---|---|---|
| 4,016,218 A | 4/1977 | Haag et al. | |
| 4,171,257 A | 10/1979 | O'Rear et al. | |
| 4,234,412 A | 11/1980 | Boersma et al. | |
| 4,251,348 A | 2/1981 | O'Rear et al. | |
| 4,361,503 A | 11/1982 | Dwyer et al. | |
| 4,417,086 A | 11/1983 | Miller | |
| 6,069,287 A | 5/2000 | Ladwig et al. | |
| 6,455,750 B1 | 9/2002 | Steffens et al. | |

FOREIGN PATENT DOCUMENTS

| | | |
|---|---|---|
| EP | 0757969 B1 | 2/1997 |
| EP | 1 036 137 B1 | 9/2000 |
| EP | 1 036 139 B1 | 9/2000 |

*Primary Examiner*—Thuan D Dang
(74) *Attorney, Agent, or Firm*—Burns, Doane, Swecker & Mathis, L.L.P.

(57) ABSTRACT

The present invention is directed to a process for upgrading Fischer-Tropsch products comprising oxygenates, $C_{6+}$ olefins, and optionally heteroatom impurities such as nitrogen compounds, by contacting the product stream with acidic olefin cracking catalyst. This acidic olefin cracking catalyst converts the oxygenates and $C_{6+}$ olefins in the Fischer-Tropsch product to form valuable light olefins such as propylene, butenes, and some pentenes, while leaving paraffins in the Fischer-Tropsch product largely unreacted. The light olefins formed can easily be separated and used for a variety of purposes.

31 Claims, 1 Drawing Sheet

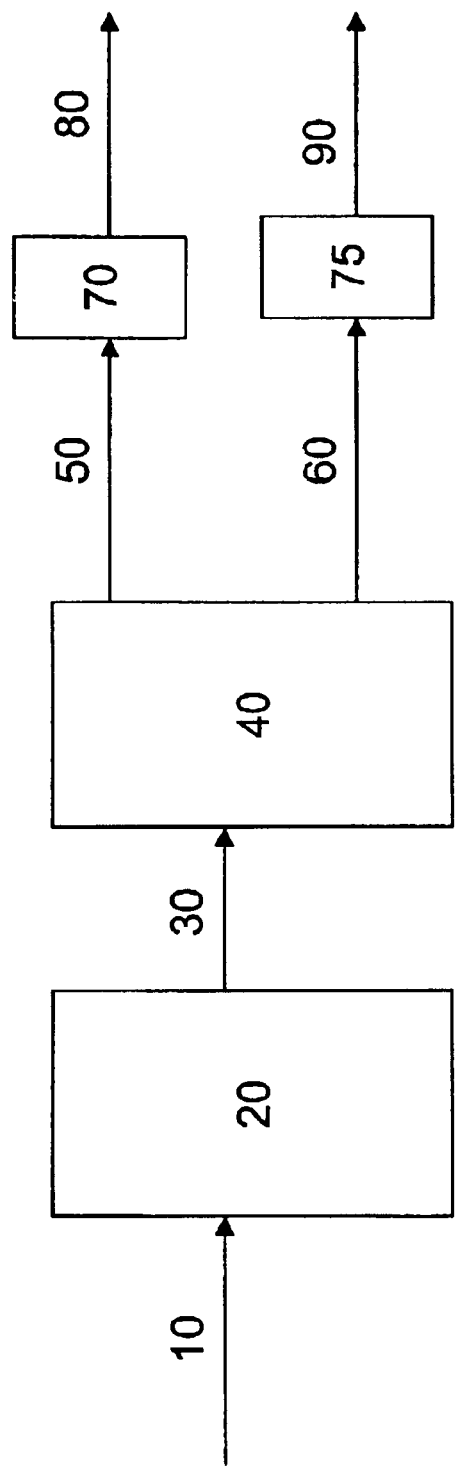
FIGURE

PROCESS TO UPGRADE FISCHER-TROPSCH PRODUCTS AND FORM LIGHT OLEFINS

FIELD OF THE INVENTION

The present invention is directed to a novel process for upgrading Fischer-Tropsch products, and more particularly to a novel process for upgrading Fischer-Tropsch products, thereby forming light olefins.

BACKGROUND OF THE INVENTION

Fischer-Tropsch products typically are rich in linear paraffins, but often are contaminated with oxygenates, olefins, and on occasion traces of nitrogen compounds. These contaminants are generally not desirable in salable products, such as diesel fuel, paraffinic naphtha, jet fuel, liquefied petroleum gas (LPG), solvents, aromatics, lube base stock, and combinations thereof, so they must be removed by upgrading processes.

The most common upgrading process is hydroprocessing. Hydroprocessing is a general term meant to include more specific technologies such as hydrotreating, hydrocracking, hydroisomerization, reforming, and hydrodewaxing. Hydroprocessing in general converts oxygenates and olefins into additional paraffins and removes heteroatom compounds, such as nitrogen compounds. Hydroprocessing is performed by contacting a feed over a catalyst that contains a metal in the presence of hydrogen at pressures and temperatures greater than ambient. While olefins in Fischer-Tropsch products can contribute to the formation of carbon deposits on hydroprocessing catalysts, thus poisoning them, these catalysts can be regenerated by burning the carbon deposits. However, regeneration typically operates at elevated pressures. Therefore, regeneration requires expensive facilities to conduct in-situ regeneration, or facilities to load and unload the catalysts from the hydroprocessing reactor and regenerate the catalysts off-site.

In addition, almost all hydroprocessing technologies require the use of hydrogen gas as a reactant. This hydrogen gas is expensive to obtain and to store. Reforming is the only hydroprocessing technology that does not require the continued consumption of expensive hydrogen gas. Although reforming does not require the consumption of hydrogen, reforming does require pretreatment of the feed by hydrotreating to remove any oxygenates and heteroatom compounds, such as nitrogen compounds. When reforming is used to convert Fischer-Tropsch products, typically $C_6$-$C_{10}$ products, to benzene, toluene, xylene, and other aromatics, the catalyst typically comprises platinum on an alumina support in the presence of a halogen, commonly chloride. The chloride is essential to operation of the reforming catalyst. However, if the feed contains oxygenates and any residual nitrogen compounds, the oxygenates strip the chloride from the catalyst, forming water, and the nitrogen compounds react with the chloride forming volatile ammonium chloride. The volatile ammonium chloride leaves the reactor and can cause corrosion problems in downstream equipment. Therefore, pretreatment of the feed to remove oxygenates and nitrogen compounds is especially important when reforming is used as the upgrading process. Typically a hydroprocessing unit, such as a hydrotreater, upstream of the reformer, is used to accomplish this pretreatment.

Upgrading processes for hydrocarbon feeds, including processes for petroleum feeds and processes for Fischer-Tropsch feeds, are known in the art. By way of example, U.S. Pat. Nos. 4,171,257 and 4,251,348 relate to processes for upgrading a petroleum distillate feed. In this upgrading process, the petroleum feed, containing a significant content of normal paraffins, is dewaxed with ZSM-5 zeolite, and the effluent product stream is fractionated producing a $C_3$-$C_4$ olefin product fraction.

U.S. Pat. No. 4,234,412 relates to a process for upgrading a reaction product obtained in a Fischer-Tropsch hydrocarbon synthesis. The process comprises separating the product into at least one of a light boiling fraction and/or heavy boiling fraction and contacting the fraction(s) with certain crystalline silicates to obtain an aromatic gasoline and/or a fuel oil having a lowered pour point.

U.S. Pat. Nos. 6,455,750 and 6,069,287 relate to a process for producing light olefins from a catalytically cracked or thermally cracked naphtha stream. The cracked naphtha, which contains 10 to 30 wt % paraffins and 20 to 70 wt % olefins, is cracked with a catalyst containing a crystalline zeolite having an average pore diameter less than about 0.7 nanometers at reaction conditions.

U.S. Pat. No. 4,361,503 relates to an improved process for converting synthesis gas to hydrocarbon mixtures using an improved catalyst composition. The catalyst comprises an iron-containing, Fischer-Tropsch catalyst and a crystalline zeolite having a silica-to-alumina ratio of greater than 200 (including zeolites containing essentially no alumina) and an $(R_2O+M_2/nO):SiO_2$ ratio of less than 1.1:1, where M is a metal other than a metal of Group IIIA, n is the valence of the metal, and R is an alkyl ammonium radical. This process using the above catalyst composition increases the selectivity to olefinic naphtha products.

PCT application WO 00/53695 relates to an environmentally friendly gas conversion process, which produces and disposes of ammonia in the process. The gas conversion process includes producing a synthesis gas, which contains ammonia and hydrogen cyanide. The synthesis gas is used to form hydrocarbons by reacting the hydrogen and carbon monoxide in the gas in the presence of a hydrocarbon synthesis catalyst. However, the synthesis gas reversibly deactivates the catalyst due to the presence of the ammonia and hydrogen cyanide in the gas. The catalyst is rejuvenated with a gas comprising hydrogen producing an ammonia containing rejuvenation offgas. The ammonia is dissolved out of the offgas with water and then stripped out of the water with the hydrocarbon feed to the synthesis gas generator and into the generator where it is consumed. This process can contribute to the formation of nitrogen in products from the Fischer-Tropsch process.

European patent EP 0 757969B1 relates to a process for the removal of hydrogen cyanide, HCN, from synthesis gas. HCN is a poison for Fischer-Tropsch hydrocarbon synthesis processes. The HCN concentration of HCN containing synthesis gas streams is reduced by treatment with a Group IVA metal oxide and optionally containing a Group IIB, Group VA, or Group VIA metal or metals, at reaction conditions preferably suppressing Fischer-Tropsch activity. This process also can contribute to the formation of nitrogen in products from the Fischer-Tropsch process.

U.S. patent application Ser. No. 09/758,750 relates to a process for upgrading nitrogen-containing Fischer-Tropsch products using hydroprocessing. U.S. patent application Ser. No. 09/758,751 relates to the use of chemical analysis of Fischer-Tropsch waxes, in particular, the determination of heteroatom content, including nitrogen, in Fischer-Tropsch waxes.

Accordingly, efficient and inexpensive processes to reduce or eliminate olefin, oxygenate, and heteroatom compound impurities in Fischer-Tropsch products are desired, while at the same time converting as much of the Fischer-Tropsch products to form valuable products as is possible. Therefore, efficient and inexpensive processes to convert the olefin and oxygenate impurities to form more valuable products are also desired.

SUMMARY OF THE INVENTION

A process for upgrading a Fischer-Tropsch product comprising paraffins, oxygenates, and $C_{6+}$ olefins is disclosed. The process includes contacting the Fischer-Tropsch product with an acidic olefin cracking catalyst to convert the oxygenates and $C_{6+}$ olefins to form light olefins. The contacting conditions include a temperature in the range of about 500° F. to 850° F., a pressure below 1000 psig, and a liquid hourly space velocity in the range of from about 1 to 20 $hr^{-1}$. The process further includes recovering the Fischer-Tropsch product comprising unreacted paraffins, and recovering the light olefins.

In another embodiment, a process for producing saleable products from a Fischer-Tropsch product stream is disclosed. The process includes producing a Fischer-Tropsch product stream comprising paraffins, oxygenates, and $C_{6+}$ olefins. The Fischer-Tropsch product stream is contacted with an acidic olefin cracking catalyst to convert the oxygenates and $C_{6+}$ olefins to form light olefins, providing a stream comprising light olefins and unreacted paraffins. The contacting conditions include a temperature in the range of about 500° F. to 850° F., a pressure below 1000 psig, and a liquid hourly space velocity in the range of from about 1 to 20 $hr^{-1}$. The unreacted paraffins and light olefins are separated. The light olefins are recovered and a salable product is produced from the light olefins. The salable product produced from the light olefins may be commercial grade propylene, high octane gasoline blend components, polypropylene, polyisobutylene, isooctane, cumene, isopropyl alcohol, tertiary butyl alcohol, methyl tertiary-butyl ether, tertiary-amyl methyl ether, ethyl tertiary-butyl ether, and tertiary-amyl ethyl ether, and combinations thereof. The unreacted paraffins are recovered and a salable product is produced from the unreacted paraffins. The salable product produced from the unreacted paraffins may be diesel fuel, paraffinic naphtha, jet fuel, liquefied petroleum gas, solvents, lube base stock, and combinations thereof.

In yet another embodiment, a process for upgrading a Fischer-Tropsch product comprising paraffins, oxygenates, and $C_{6+}$ olefins is disclosed. The process includes contacting the Fischer-Tropsch product with an acidic olefin cracking catalyst to convert the oxygenates and $C_{6+}$ olefins to form light olefins, providing an effluent comprising unreacted paraffins and light olefins. The contacting conditions include a temperature in the range of about 500° F. to 850° F., a pressure below 1000 psig, and a liquid hourly space velocity in the range of from about 1 to 20 $hr^{-1}$. The effluent is cooled to convert the unreacted paraffins into a liquid and the unreacted liquid paraffins are recovered. The process includes further cooling the effluent to convert at least a portion of the light olefins into a liquid and recovering the light olefins.

BRIEF DESCRIPTION OF THE DRAWING

The FIGURE is a schematic flow diagram of one embodiment of the invention.

DETAILED DESCRIPTION OF THE INVENTION

The product from a Fischer-Tropsch process often contains $C_{6+}$ olefins, oxygenates, and heteroatom impurities. The process of the present invention upgrades a Fischer-Tropsch product stream comprising paraffins, oxygenates, and $C_{6+}$ olefins and optionally heteroatom impurities, such as nitrogen containing compounds. According to the present invention, it has been found that oxygenates and $C_{6+}$ olefins in Fischer-Tropsch products can be converted to form light olefins using an acidic olefin cracking catalyst. In addition, it has been found that any nitrogen impurities in the Fischer-Tropsch product can also be removed using the acidic cracking catalyst. The acidic olefin cracking catalysts of the present invention selectively convert oxygenates and $C_{6+}$ olefins to form light olefins. Accordingly, oxygenates and $C_{6+}$ olefins are quite reactive over the catalysts used in the processes of the present invention, while paraffins are less reactive. Both cracking and dehydration converts oxygenates to form light olefins. Cracking converts $C_{6+}$ olefins to form light olefins.

Accordingly, the process of the present invention converts oxygenates and $C_{6+}$ olefins in a Fischer-Tropsch product to form valuable products. The light olefins have a higher value than the heavier $C_{6+}$ olefins; therefore, it is advantageous to convert the oxygenates and $C_{6+}$ olefins to form light olefins. Therefore, the process of the present invention provides additional valuable products from a Fischer-Tropsch product.

In addition, the process of the present invention converts oxygenates and $C_{6+}$ olefins in the Fischer-Tropsch product stream to form light olefins, removes nitrogen impurities, and leaves paraffins largely unconverted or unreacted in a single processing step. In the present invention the Fischer-Tropsch product is contacted with an acidic olefin cracking catalyst under contacting conditions including a temperature in the range of about 500° F. to 850° F., a pressure below 1000 psig, and a liquid hourly space velocity in the range of from about 1 to 20 $hr^{-1}$. As provided this process is a simple single stage process and accordingly has both cost and efficiency advantages over an upgrading process that requires a nitrogen and/or oxygenate pretreatment and a catalytic conversion section.

For purposes of the present invention, the following definitions will be used herein:

Fischer-Tropsch products are products that originate from, or are produced at some stage by, a Fischer-Tropsch process.

The Constraint Index is described in U.S. Pat. No. 4,016, 218 and can be used to measure the activity and stability of the acidic olefin cracking catalyst. The Hydrogen Transfer activity of the catalyst may also be measured by the procedure described in U.S. Pat. No. 4,417,086. The Constraint Index conversion is defined as the disappearance of the feedstock hexane isomers under the Constraint Index test described in U.S. Pat. No. 4,016,218.

Light olefins consist essentially of propylene, butenes, and smaller amounts of pentenes. Light olefins, as defined by the present invention, have a molar ratio of propylene to propane of >1, preferably >2, and most preferably >5. The butenes and pentenes in the light olefins, formed in the processes of the present invention, are rich in internal isoolefins such as isobutene and 2-methyl-2-butene. Olefins of this type are quite different from the olefins typically found in Fischer-Tropsch products, which are predominantly linear primary olefins. Light olefins, as defined by the present invention, are comprised of >50 wt %, preferably >60 wt %, and more preferably >70 wt %, $C_{3-4}$ hydrocarbons.

Light olefins, as defined by the present invention, contain less than 10 ppm, preferably less than 2 ppm, and more preferably less than 1 ppm, of each sulfur and nitrogen impurities, and less than 500 ppm, preferably less than 100 ppm, more preferably less than 50 ppm, oxygen as oxygenates (alcohols, acids, ketones, etc.) on an air- and water-free basis. Light olefins also contain less than 2000 ppm, preferably less than 1000 ppm, and more preferably less than 100 ppm, total diolefin and acetylenic impurities. These low levels of impurities make light olefin streams significantly more pure than typical olefin streams produced in conventional refinery processes such as Fluidized Bed Catalytic Cracking and Coking, facilitating their use in further upgrading operations. Finally, light olefins contain less than 10 wt %, preferably less than 5 wt %, and more preferably less than 2.5 wt %, of $C_2$ and lighter ($C_{2-}$) hydrocarbons. The low levels of $C_2$ and $C_{2-}$ hydrocarbons permit the recovery of light olefins from the gaseous effluent of a reactor by compression, cooling, and condensation at moderate conditions.

Unconverted or unreacted paraffins are those paraffins in the Fischer-Tropsch products that are not converted to lower molecular weight products as a result of contact over the acidic olefin cracking catalysts used in the processes of the present invention.

Fischer-Tropsch

The present invention is directed to a novel process for upgrading products formed from a Fischer-Tropsch process. In Fischer-Tropsch chemistry, syngas is converted to liquid hydrocarbons by contact with a Fischer-Tropsch catalyst under reactive conditions. Typically, methane and optionally heavier hydrocarbons (ethane and heavier) can be sent through a conventional syngas generator to provide synthesis gas. Generally, synthesis gas contains hydrogen and carbon monoxide, and may include minor amounts of carbon dioxide and/or water. The presence of sulfur, nitrogen, halogen, selenium, phosphorus and arsenic contaminants in the syngas is undesirable. For this reason and depending on the quality of the syngas, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art. It also may be desirable to purify the syngas prior to the Fischer-Tropsch reactor to remove carbon dioxide produced during the syngas reaction and any additional sulfur compounds not already removed. This can be accomplished, for example, by contacting the syngas with a mildly alkaline solution (e.g., aqueous potassium carbonate) in a packed column.

In the Fischer-Tropsch process, contacting a synthesis gas comprising a mixture of $H_2$ and CO with a Fischer-Tropsch catalyst under suitable temperature and pressure reactive conditions forms liquid and gaseous hydrocarbons. The Fischer-Tropsch reaction is typically conducted at temperatures of about 300–700° F. (149–371° C.), preferably about 400–550° F. (204–228° C.); pressures of about 10–600 psia, (0.7–41 bars), preferably about 30–300 psia, (2–21 bars); and catalyst space velocities of about 100–10,000 cc/g/hr, preferably about 300–3,000 cc/g/hr. Examples of conditions for performing Fischer-Tropsch type reactions are well known to those of skill in the art.

The products of the Fischer-Tropsch synthesis process may range from $C_1$ to $C_{200+}$ with a majority in the $C_5$ to $C_{100+}$ range. The reaction can be conducted in a variety of reactor types, such as fixed bed reactors containing one or more catalyst beds, slurry reactors, fluidized bed reactors, or a combination of different type reactors. Such reaction processes and reactors are well known and documented in the literature.

In general, Fischer-Tropsch catalysts contain a Group VIII transition metal on a metal oxide support. The catalysts may also contain a noble metal promoter(s) and/or crystalline molecular sieves. Certain catalysts are known to provide chain growth probabilities that are relatively low to moderate, and the reaction products include a relatively high proportion of low molecular ($C_{2-8}$) weight olefins and a relatively low proportion of high molecular weight ($C_{30+}$) waxes. Certain other catalysts are known to provide relatively high chain growth probabilities, and the reaction products include a relatively low proportion of low molecular ($C_{2-8}$) weight olefins and a relatively high proportion of high molecular weight ($C_{30+}$) waxes. Such catalysts are well known to those of skill in the art and can be readily obtained and/or prepared.

The product from a Fischer-Tropsch process contains predominantly paraffins; however, it may also contain $C_{6+}$ olefins, oxygenates, and heteroatom impurities. The most abundant oxygenates in Fischer-Tropsch products are alcohols, and mostly primary linear alcohols. Less abundant types of oxygenates in Fischer-Tropsch products include other alcohol types such as secondary alcohols, acids, esters, aldehydes, and ketones.

A Fischer-Tropsch product containing no or minimal $C_{6+}$ olefins, oxygenates, and heteroatom impurities is ultimately desired.

Acidic Olefin Cracking Catalysts

An upgrading process or processes typically are used to convert the Fischer-Tropsch products to salable products. It has been discovered that a Fischer-Tropsch product can be upgraded to reduce or eliminate $C_{6+}$ olefins, oxygenates, and optionally heteroatom impurities, by contact with an acidic olefin cracking catalyst. Accordingly, in the present invention, a Fischer-Tropsch product containing paraffins, oxygenates, $C_{6+}$ olefins, and optionally heteroatom impurities, such as nitrogen-containing compounds, is contacted with an acidic olefin cracking catalyst under the below-specified conditions.

The acidic olefin cracking catalysts used in the processes of the present invention selectively convert $C_{6+}$ olefins, while leaving paraffins largely unreacted. The selectivity of the acidic olefin cracking catalysts should be high and thus, the $C_{6+}$ olefins should crack more readily using the catalysts than paraffins of the same carbon number. In addition, the hydrogenation and hydrogen transfer activity of the catalysts should be low. The acidic olefin cracking catalyst also preferably removes at least a portion of any nitrogen-containing impurities. Moreover, the catalysts used in the processes of the present invention preferably are stable during use. As stated, the key features of the acidic olefin cracking catalysts used in the processes of the present invention is that they have sufficient activity and stability during cracking reactions that produce olefinic products.

The acidic olefin cracking catalysts used in the processes of the present invention include zeolites, preferably zeolites containing 10-ring pores more preferably ZSM-5, ZSM-11, ZSM-22, ZSM-23, and most preferably ZSM-5 or ZSM-11. With regards to ZSM-5 and ZSM-11, preferred are ZSM-5 and ZSM-11 of $SiO_2/Al_2O_3$ molar ratio greater than 200, and more preferred are ZSM-5 and ZSM-11 of $SiO_2/Al_2O_3$ molar ratio greater than 500. Preferred acidic olefin cracking catalysts are intermediate pore zeolite catalysts. Intermediate pore zeolite catalysts have an effective pore aperture in the range of about 5 to 6.5 Angstroms when the molecular sieve is in the H-form. Molecular sieves having pore apertures in this range tend to have unique molecular sieving characteristics. Unlike small pore size zeolites such as erionite and chabazite, they will allow hydrocarbons having some branching into the molecular sieve void spaces. Unlike larger pore size zeolites such as the faujasites, they can differentiate between n-alkanes and slightly branched alkanes on the one hand and larger branched alkanes having, for example, quaternary carbon atoms.

The activity and stability of the acidic olefin cracking catalyst may be described by specifying a conversion at a reaction temperature, as measured in the Constraint Index test using hexanes. The Constraint Index of a catalyst is as described in U.S. Pat. No. 4,016,218, the entire disclosure of which is incorporated herein by reference for all purposes. As a measure of activity, the acidic olefin cracking catalysts of the present invention have a Constraint Index conversion at 10 minutes of >20% at 800° F., preferably a Constraint Index conversion at 10 minutes of >20% at 700° F., and more preferably a Constraint Index conversion at 10 minutes of >40% at 600° F. As a measure of stability, the acidic olefin cracking catalysts of the present invention have a decline in Constraint Index conversion from 180 to 10 minutes of <30%, preferably <20%, and more preferably <10%.

The decline in Constraint Index conversion is measured by the following formula:

Decline =100*(% Initial Conversion–% Final Conversion)/(% Initial Conversion)

Table I, below, summarizes Constraint Index test results for a series of zeolite catalysts.

TABLE 1

Constraint Index Test Results

| Zeolite Structure Type | ZSM-11 | ZSM-5 | Beta | ZSM-12 | ZSM-12 | Y-Zeolite |
|---|---|---|---|---|---|---|
| Pore Size | 10-ring | 10-ring | 12-ring | 12-ring | 12-ring | 12-ring |
| Temp., ° F. | 600 | 600 | 600 | 600 | 700 | 600 |
| Conv. @ 10 min | 97.9 | 44.1 | 95.6 | 7.8 | 83.7 | 84.9 |
| Conv. @ 430 min. | 98.1 | 41.7 | 16.6 | 4.5 | 16.9 | 31.5 |
| Decline in Constraint Index Conversion | −0.2 | 5.4 | 82.6 | 42.3 | 79.8 | 62.9 |

While all materials tested exhibited sufficient activity, only the ZSM-5 and ZSM-11 samples exhibited the desired stability, with a decline in Constraint Index conversion of <30%.

Catalysts, which do not possess stabilities as measured by a decline in Constraint Index conversion from 180 to 10 minutes of <30%, will require frequent regeneration and thus are not preferred for use in the processes of the present invention. Catalysts that exhibited the desired stability are zeolites having 10-ring pores and the catalysts that exhibited less than the desired stability are zeolites having 12-ring pores.

The acidic olefin cracking catalysts of the present invention can contain other components in addition to the active catalyst component. For example, the acidic olefin cracking catalysts of the present invention can contain binders.

In the acidic olefin cracking catalysts of the present invention, metal components are not necessary. However, while metals are not necessary in the catalysts, metals may be used to assist in oxidative regeneration to remove carbon deposits.

The acidic olefin cracking catalysts of the present invention are typically in a formed shape, such as an extrudate. The content of zeolite in bound catalysts is 1–99 wt %, preferably 10–90 wt %, and more preferably 25–75 wt %.

Reaction Conditions for the Upgrading Process

The upgrading process of the present invention is performed by contacting the Fischer-Tropsch product containing paraffins, oxygenates, $C_{6+}$ olefins, and optionally heteroatom impurities, such as nitrogen-containing compounds, with an acidic olefin cracking catalyst.

The olefin cracking reaction of the Fischer-Tropsch product is endothermic, and if the olefin content in the Fischer-Tropsch product is high enough, the reaction may cool to the point that the reaction stops. Thus, the use of several reactors in series with intermediate reheating may be required. A variety of reactors may be used. Designs of types of reactors that may be used include fixed bed upflow reactors, fixed bed downflow reactors, and fluidized bed reactors. The preferred reactor design is a downflow fixed bed reactor. Heat for the reaction can be provided by furnaces, or by use of heat generated elsewhere in the process, for example, the methane reformer.

Operation at pressures near atmospheric is desired because it favors the formation of propylene and butene, as opposed to higher molecular weight olefins. Also, when pressures greater than atmospheric are used, a secondary reaction can occur. This secondary reaction is a hydrogen transfer or conjunct polymerization reaction and it can convert a portion of the olefinic product into aromatics and isoparaffins. As products, aromatics and isoparaffins, are less valuable in comparison to the light olefins. Therefore, it is generally desirable to limit the hydrogen transfer reaction by operating at low pressures. Hydrogen transfer can also be limited by reducing the acidity of the catalyst. This is done by using materials that are rich in silica relative to alumina, that is, $SiO_2/Al_2O_3$ molar ratios of >50 preferably >200, more preferably >500, and most preferably >1000. Hydrogen transfer can also be limited by partial neutralization of the acidity of the zeolite such as by exchange with a Group IA or IIA metal.

While it is preferred to operate at a pressure as close to atmospheric pressure as practical, operation at precisely atmospheric pressure may not be optimum for the process of the present invention because at atmospheric pressure, a significant portion of the Fischer-Tropsch products may vaporize. Preventing vaporization of the Fischer-Tropsch products at atmospheric pressure would require significant cooling and thus involve the use of a large amount of energy not all of which would be recoverable in downstream heat exchangers. Therefore, as a consequence of efficiency due to energy conservation, it is preferable to operate the process of the present invention at a pressure that is slightly higher than atmospheric.

It is also desirable to operate the process of the present invention at higher than atmospheric pressure for reasons in addition to energy conservation. At pressures slightly higher than atmnospheric, the propylene and butene products can be recovered by condensation rather than by compression. Recovery by condensation greatly simplifies the recovery process. The optimum operating pressure of the process of the present invention will depend upon the boiling range of the Fischer-Tropsch products and the desired light olefin products. However, in general the pressure is <1000 pounds per square inch gauge (psig), preferably <100 psig, more preferably 0–50 psig, and most preferably 20–40 psig.

In the process of the present invention, addition of a diluent gas can be used to effectively reduce the partial pressure of the light olefin products and reduce the extent of hydrogen transfer. The diluent gas utilized can be $H_2$, $N_2$, $CH_4$, $CO_2$, $H_2O$, and combinations thereof. In the process of the present invention, the amount of diluent gas typically used is <10,000 standard cubic feet per barrel (SCFB), preferably <5,000 SCFB, more preferably <1,000 SCFB, and most preferably, a diluent gas is not used at all.

The olefin cracking reaction of the present invention is operated at a temperature of 500–850° F. In addition, the olefin cracking reaction of the present invention is operated at a liquid hourly space velocity (LHSV) of >0.25 $hr^{-1}$, preferably 1–20 $hr^{-1}$, and more preferably 2–10 $hr^{-1}$.

In the upgrading process of the present invention, when the oxygenates contained in a Fischer-Tropsch product are contacted with the acidic olefin cracking catalyst under conditions as described above, the oxygenates are quickly converted. The oxygenates react to form water and may form olefins.

In the upgrading process of the present invention, the basic reaction of the $C_{6+}$ olefins contained in a Fischer-Tropsch product when contacted with the acidic olefin cracking catalyst under conditions as described above is one of cracking. Cracking of the $C_{6+}$ olefins can be viewed as a redistribution of the $C_{6+}$ olefins to all possible olefin isomers and olefin species within the constraints of a thermodynamic equilibrium. Therefore, the change in distribution of the olefins in the product can be predicted in general terms by the conditions of the reaction, such as temperature and pressure. Operation at relatively high temperature, >750° F., or at pressures near atmospheric, favors the formation of lighter olefins such as propylene. Operation at relatively lower temperatures, <750° F., and pressures above atmospheric, 100–500 psig, favors the formation of butene and pentenes. Due to unfavorable thermodynamics, significant quantities of ethylene are not formed under usual process conditions. Likewise, due to thermodynamic considerations, $C_4$ and heavier olefins predominantly will contain double bonds at internal positions and frequently will be methyl branched. As an example, butenes will typically consist of >25 wt % isobutene, and more typically >35 wt % isobutene. The exact proportions of any individual olefin species will depend on the specific temperature and pressure conditions of the particular reaction. The distribution can be estimated from thermodynamic equilibrium calculations.

Since the reaction among the olefins approaches an equilibrium distribution, it is possible to recycle unwanted olefins back to the reactor and have them converted into desired olefins. In this way, the yield of the most desirable olefins can be increased. For example, if it is desired to sell propylene and convert isobutylene into polyisobutylene, normal butenes and pentenes can be recycled to the reactor and converted into additional propylene and isobutylene.

The process of the present invention selectively converts the oxygenates and $C_{6+}$ olefins contained in the Fischer-Tropsch product to form light olefins while leaving the paraffins contained in the Fischer-Tropsch product largely unconverted. Accordingly, the oxygenates and $C_{6+}$ olefins contained in the Fischer-Tropsch product are quite reactive over the catalysts in the process of the present invention; however, the paraffins contained in the Fischer-Tropsch product are less reactive over the catalysts under the conditions of the process of the present invention.

The conversion of oxygenates and $C_{6+}$ olefins contained in the Fischer-Tropsch product in the process of the present invention is >25 wt %, preferably >50 wt %, and more preferably >80 wt %. Most preferably, the oxygenates are converted to below the level of detection. The percentages provided refer to a combined conversion of oxygenates and $C_{6+}$ olefins, such that individually, the conversion of oxygenates or $C_{6+}$ olefins may fall below the desired level. Stated otherwise, the conversion of, for example, $C_{6+}$ olefins might be <25%, so long as the conversion of oxygenates and $C_{6+}$ olefins is >25%. The conversion of paraffins to lower molecular weight products is always less than the conversion of the oxygenates and $C_{6+}$ olefins. On an absolute basis, the conversion of the paraffins contained in the Fischer-Tropsch product is preferably <50 wt %, more preferably <25 wt %, and most preferably <10 wt %.

Conversion, as defined in the present invention, is measured by a reduction or disappearance of a component from the initial feed to the product stream. Conversion is expressed as a ratio of the amount of a component, such as oxygenates and/or $C_{6+}$ olefins, in the product stream of the process to the amount of that component in the feed to that process. According to the present invention, oxygenates and/or $C_{6+}$ olefins, present in the feed to the upgrading process of the present invention, are reduced in or disappear from the product stream generated. The net effect of the present invention is generation of light olefins and reduction of oxygenates and $C_{6+}$ olefins. Accordingly, the reduction or disappearance of oxygenates and/or $C_{6+}$ olefins may occur through a single reaction or a series of reactions to form light olefins.

Fischer-Tropsch products may contain nitrogen-containing compounds. Nitrogen is not always an impurity in Fischer-Tropsch products, but when it is present in the present invention, it is present in an amount of >0.2 parts per million by weight (wppm), preferably >1 wppm, more preferably >5 wppm, and most preferably >10 ppm.

The process of the present invention, in addition to converting oxygenates and $C_{6+}$ olefins to form light olefins, removes nitrogen impurities from the Fischer-Tropsch stream. The percentage of nitrogen removed from a Fischer-Tropsch stream containing nitrogen impurities will be >25 wt %, preferably >50 wt %, and more preferably >90 wt %, calculated by comparing the content of nitrogen in the Fischer-Tropsch product stream prior to and following the process of the present invention.

In the process of the present invention, the acidic olefin cracking catalyst converts nitrogen compounds in the Fischer-Tropsch product stream, thus removing nitrogen impurities from the light olefins, as well as from the unreacted paraffins. If necessary, the catalyst can be regenerated by oxidation, typically by contacting the catalysts with dilute air at elevated temperatures to combust carbon deposits and simultaneously remove nitrogen deposits.

Separation and Purification of the Light Olefins

The light olefins formed using the process of the present invention typically are comprised of approximately 5–95 wt %, preferably 10–85 wt %, and more preferably 35–75 wt %, propylene; approximately 5–95wt %, preferably 10–85 wt %, and more preferably 35–75 wt %, butanes; and approximately 0.1–35 wt %, preferably 1–20 wt %, and more preferably 2.5–10 wt %, pentenes.

The separation and purification of the light olefins from the unreacted paraffins can be accomplished by conventional methods of condensation. There is an advantage to the recovery of the light olefins from the processes of the present invention in comparison to the recovery of light olefins from a typical process like fluidized bed catalytic cracking (FCC). In the FCC process, light olefins are produced along with light gases such as methane, ethane, hydrogen, hydrogen sulfide, and ethylene. As the light gases are mixed with the light olefins and heavier olefins, it is difficult or impossible to recover the light olefins from a FCC process by cooling the gas until it forms a liquid. Thus, the FCC process requires an expensive compressor, commonly called a wet gas compressor, to compress the gas stream so that it can be converted to a liquid by cooling.

In contrast, the gases from the processes of the present invention will contain very small quantities of the above-mentioned light gases and no hydrogen sulfide. Thus, the light olefins from the processes of the present invention can be converted to a liquid by cooling without the need for compression.

A preferred separation scheme of the present invention involves taking the effluent from the olefin cracking unit and first cooling it to the point that the unreacted paraffins, which are in the gas phase, are predominantly converted to a liquid. The remaining gas, which includes propylene, butenes, and other components, is then further cooled to convert at least a portion, and preferably a majority, of the propylene and butenes into a liquid. Water formed from the reaction of the oxygenates will also condense and be collected with both the light olefins arid unreacted paraffins. The water can be separated from these hydrocarbon products due to density differences. The hydrocarbon liquid is then compressed and sent to a series of distillation columns and separators from which purified light olefins can obtained. Compression of a liquid is much less costly in terms of equipment and energy consumption costs than is compression of a gas. Any remaining uncondensed gas can be compressed and sent to the series of distillation columns and separators, or if the olefin content is low enough, simply used directly as fuel.

Salable Products

Unconverted or unreacted paraffins recovered from the process of the present invention may be used to make diesel fuel, paraffinic naphtha, jet fuel, liquefied petroleum gas (LPG), solvents, lube base stock, and combinations thereof. The unreacted paraffins may be used directly as such in salable products or upgraded by any number of conventional processes. Upgrading processes include hydrotreating, hydrocracking, hydroisomerization, reforming, catalytic dewaxing, solvent dewaxing, adsorbent treating, and catalytic cracking.

The light olefins formed and recovered in the processes of the present invention can be used in a variety of conventional processes to make salable propylene of commercial or polymerization purities, high octane gasoline blend components such as isoparaffin alkylate, polymers such as polypropylene, polyisobutylene, and isooctane, cumene and other alkyl aromatics, alcohols such as isopropyl alcohol and tertiary butyl alcohol, ethers such as methyl tertiary-butyl ether (MTBE), tertiary-amyl methyl ether (TAME), ethyl tertiary-butyl ether (ETBE), and tertiary-amyl ethyl ether (TAEE), and combinations thereof. These conventional processes include polymerization, oligomerization, etherification, aromatic-olefin alkylation, isoparaffin-olefin alkylation, and hydration.

Preferred Embodiment

Referring to the FIGURE, a Fischer-Tropsch product (10) comprising paraffins, oxygenates, $C_{6+}$ olefins, and optionally nitrogen is fed to a cracking zone (20) containing an acidic olefin cracking catalyst under conditions including a temperature in the range of about 500° F. to 850° F., a pressure below 1000 psig, and an LHSV in the range of from about 1 to 20 hr$^{-1}$. A product stream (30) comprising unreacted paraffins is recovered from the cracking zone (20) and sent to a separation zone (40) wherein light olefins (50) and unreacted paraffins (60) are separated. Finally, the light olefins (50) and unreacted paraffins (60) are sent to upgrading processes (70) and (75), respectively, producing salable products (80) and (90), respectively.

The following examples are given to illustrate the invention and should not be construed to limit the scope of the invention.

EXAMPLES

A nitrogen-containing Fischer-Tropsch condensate containing three components was obtained. The properties of one of the components are detailed in Table II.

TABLE II

Properties of Fischer-Tropsch Components

| Property | |
|---|---|
| Gravity, ° API | 56.8 |
| Sulfur, ppm | <1 |
| Oxygen, ppm by Neut. Act. | 1.58 |
| Nitrogen, ppm | 10 |
| Chemical Types, Wt % by GC-MS | |
| Paraffin | 38.4 |
| Olefin | 49.5 |
| Alcohol | 11.5 |
| Other | 0.5 |
| Distillation by D-2887, ° F. by wt % | |
| 0.5/5 | 80/199 |
| 10/30 | 209/298 |
| 50 | 364 |
| 70/90 | 417/485 |
| 95/99.5 | 518/709 |

In addition to about 50 wt % olefins, the feedstock contains approximately 11 wt % alcohols. Gas chromatography-mass spectrometry (GC-MS) shows that nearly all the olefins are 1-alphaolefins, as expected for Fischer-Tropsch stocks.

Light Olefins from Olefin Cracking of Fischer-Tropsch Products

For this test, a ZSM-5 catalyst (35 wt % alumina binder), in which the silica/alumina molar ratio ($SiO_2/Al_2O_3$ molar ratio) of the zeolite was 300, in order to minimize hydrogen transfer, was used. No metal was added to the catalyst. The test was run in the absence of added $H_2$ and at low pressure, again to minimize hydrogen transfer.

Results at two different conversion levels are given in Table III. At the lower temperature (600° F.) and low conversion, the production of light olefins through cracking was quite selective. Essentially all of the alcohols were converted to olefins.

At the higher temperature (650° F.) and high conversion, most of the cracked product was olefinic, although the selectivity was less than it was at lower conversion. In addition, aromatics, primarily alkyl-aromatics, were clearly evident by GC-MS in the $C_{7+}$ region, indicative of hydrogen transfer.

The feedstock nitrogen content is reduced from its initial value of 10 ppm to 0.1–0.22 ppm simultaneously to the conversion of the feedstock olefins and formation of the light olefin product. Over 97% of the nitrogen was removed.

TABLE III

Cracking of Fischer-Tropsch $C_5$-500° F. Feed over ZSM-5 (300 $SiO_2/Al_2O_3$ molar ratio) at 2.0 LHSV and 40 psig

| Reactor-Temperature, ° F. | 600 | 650 |
|---|---|---|
| Conversion <350° F. | 15.7 | 71.3 |
| Product Nitrogen, ppm | | 0.1–0.22 |

TABLE III-continued

Cracking of Fischer-Tropsch $C_5$-500° F. Feed over ZSM-5 (300 $SiO_2/Al_2O_3$ molar ratio) at 2.0 LHSV and 40 psig

| Reactor-Temperature, ° F. | 600 | 650 |
|---|---|---|
| Yields, Wt % | | |
| Ethylene | 0.06 | 0.16 |
| Propylene | 0.67 | 2.67 |
| Propane | 0.05 | 1.00 |
| Butenes | 0.28 | 3.66 |
| Butanes | 0.05 | 1.51 |
| $C_5$-180° F. | 9.06 | 32.07 |
| 180–350° F. | 44.93 | 43.63 |
| 350–550° F. | 42.24 | 14.49 |
| 550° F+ | 2.67 | 0.81 |
| HC Type, Wt %, GC-MS | | |
| Paraffin | ~30 | |
| Olefin | ~70 | |
| Alcohol | <1 | |
| Aromatics | ~0 | Evident |
| Sim. Dist, LV %, ° F. | | |
| St/5 | 14/100 | −45/17 |
| 10/30 | 157/259 | 40/154 |
| 50 | 340 | 211 |
| 70/90 | 399/482 | 292/383 |
| 95/EP | 518/665 | 424/595 |

Selectivity at high conversion could be improved by using a catalyst of lower hydrogen transfer activity. This could be accomplished by using a zeolite of higher $SiO_2/Al_2O_3$ molar ratios, preferably over 500, and more preferably over 1000. Since producing a zeolite of over 500 $SiO_2/Al_2O_3$ molar ratio is difficult and costly to do commercially due to contamination problems, treating the zeolite by hydrothermal heating, typically 500–700° C., and/or acid extraction can also lower hydrogen transfer activity.

Selectivity to form light olefins can also be improved by operating at a higher LHSV, resulting in shorter contact times, and also by operating in this mode at higher temperatures. The hydrogen transfer reaction is a secondary reaction using the products from the cracking reaction, and if the contact time is short enough, the selectivity to olefins can be improved. Increasing the temperature can maintain the conversion at the shorter contact time.

While the invention has been described in detail and with reference to specific embodiments thereof, it will be apparent to one skilled in the art that various changes and modifications can be made without departing from the spirit and scope thereof.

What is claimed is:

1. A process for upgrading a Fischer-Tropsch product comprising paraffins, oxygenates, and $C_{6+}$ olefins comprising the steps of:
   (a) contacting the Fischer-Tropsch product with an acidic olefin cracking catalyst to convert the oxygenates and $C_{6+}$ olefins to form light olefins, the contacting being under conditions including (i) a temperature in the range of about 500° F. to 850° F.; (ii) a pressure below 1000 psig; and (iii) a liquid hourly space velocity in the range of from about 1 to 20 $hr^{-1}$.
   (b) recovering the Fischer-Tropsch product comprising unreacted paraffins; and
   (c) recovering the light olefins.

2. The process of claim 1, wherein greater than 50 wt % of the oxygenates and $C_{6+}$ olefins are converted to form light olefins.

3. The process of claim 1, wherein greater than 80 wt % of the oxygenates and $C_{6+}$ olefins are converted to form light olefins.

4. The process of claim 1, wherein less than 25 wt % of the paraffins are converted to form light olefins.

5. The process of claim 1, wherein less than 10 wt % of the paraffins are converted to form light olefins.

6. The process of claim 1, wherein greater than 80 wt % of the oxygenates and $C_{6+}$ olefins are converted to form light olefins and less than 10 wt % of the paraffins are converted to form light olefins.

7. The process of claim 1, wherein the acidic olefin cracking catalyst has an activity as measured by Constraint Index conversion of >20% at 800° F. and has a stability as measured by a decline in percent Constraint Index conversion of from 180 to 10 minutes of <30%.

8. The process of claim 1, wherein the acidic olefin cracking catalyst has an activity as measured by Constraint Index conversion of >20% at 700° F. and has a stability as measured by a decline in percent Constraint Index conversion of from 180 to 10 minutes of <20%.

9. The process of claim 1, wherein the acidic olefin catalyst has an activity as measured by Constraint Index conversion of >40% at 600° F. and has a stability as measured by a decline in percent Constraint Index conversion of from 180 to 10 minutes of <10%.

10. The process of claim 1, wherein the acidic olefin cracking catalyst is a zeolite.

11. The process of claim 1, wherein the acidic olefin cracking catalyst is a zeolite having 10-ring pores.

12. The process of claim 11, wherein the acidic olefin cracking catalyst is ZSM-5 or ZSM-11.

13. The process of claim 1, wherein the acidic olefin cracking catalyst contains a binder.

14. The process of claim 1, wherein the acidic olefin cracking catalyst does not contain a metal.

15. The process of claim I, wherein the contacting is done under conditions including a pressure of less than 100 psig.

16. The process of claim 1, wherein the contacting is done under conditions including a pressure of 0–50 psig and a liquid hourly space velocity in the range of from about 2–10 $hr^{-1}$.

17. The process of claim 1, wherein the Fischer-Tropsch product further comprises nitrogen in an amount of greater than 1 wppm.

18. The process of claim 1, wherein the Fischer-Tropsch product further comprises nitrogen in an amount of greater than 5 wppm.

19. The process of claim 1, wherein the Fischer-Tropsch product further comprises nitrogen in an amount of greater than 10 wppm.

20. The process of claim 17, wherein the contacting the Fischer-Tropsch product with an acidic olefin cracking catalyst removes greater than 25 wt % of the nitrogen.

21. The process of claim 17, wherein the contacting the Fischer-Tropsch product with an acidic olefin cracking catalyst removes greater than 50 wt % of the nitrogen.

22. The process of claim 17, wherein the contacting the Fischer-Tropsch product with an acidic olefin cracking catalyst removes greater than 90 wt % of the nitrogen.

23. The process of claim 1, further comprising the step of recycling a portion of the light olefins to the contacting with an olefin cracking catalyst step.

24. A process for producing saleable products from a Fischer-Tropsch product stream comprising the steps of:
   (a) producing a Fischer-Tropsch product stream comprising paraffins, oxygenates, and $C_{6+}$ olefins;

(b) contacting the Fischer-Tropsch product stream with an acidic olefin cracking catalyst to convert the oxygenates and $C_{6+}$ olefins to form light olefins to provide a stream comprising light olefins and unreacted paraffins, the contacting being under conditions including (i) a temperature in the range of about 500° F. to 850° F.; (ii) a pressure below 1000 psig; and (iii) a liquid hourly space velocity in the range of from about 1 to 20 $hr^{-1}$;

(c) separating the unreacted paraffins and light olefins;

(d) recovering the light olefins and producing a salable product from the light olefins selected from the group consisting of commercial grade propylene, high octane gasoline blend components, polypropylene, polyisobutylene, isooctane, cumene, isopropyl alcohol, tertiary butyl alcohol methyl tertiary-butyl ether, tertiary-amyl methyl ether, ethyl tertiary-butyl ether, and tertiary-amyl ethyl ether, and combinations thereof; and (e) recovering the unreacted paraffins and producing a salable product from the unreacted paraffins selected from the group consisting of diesel fuel, paraffinic naphtha, jet fuel, liquefied petroleum gas, solvents, lube base stock, and combinations thereof.

25. The process of claim 24, wherein the Fischer-Tropsch product stream further comprises nitrogen in an amount of greater than 5 wppm and the contacting the Fischer-Tropsch product stream with an acidic olefin cracking catalyst removes greater than 90 wt % of the nitrogen.

26. The process of claim 24, wherein the acidic olefin cracking catalyst is ZSM-5 or ZSM-11.

27. The process of claim 26, wherein the acidic olefin cracking catalyst has a $SiO_2/Al_2O_3$ molar ratio of greater than 200.

28. The process of claim 27, wherein the acidic olefin cracking catalyst has a $SiO_2/Al_2O_3$ molar ratio of greater than 500.

29. A process for upgrading a Fischer-Tropsch product comprising paraffins, oxygenates, and $C_{6+}$ olefins comprising the steps of:

(a) contacting the Fischer-Tropsch product with an acidic olefin cracking catalyst to convert the oxygenates and $C_{6+}$ olefins to form light olefins to provide an effluent comprising unreacted paraffins and light olefins, the contacting being under conditions including (i) a temperature in the range of about 500° F. to 850° F.; (ii) a pressure below 1000 psig; and (iii) a liquid hourly space velocity in the range of from about 1 to 20 $hr^{-1}$;

(b) cooling the effluent to convert the unreacted paraffins into a liquid;

(c) recovering the unreacted liquid paraffins;

(d) further cooling the effluent to convert at least a portion of the light olefins into a liquid; and (e) recovering the light olefins.

30. The process of claim 29, further comprising the step of purifying the light olefins recovered in step (e) by compressing the light olefin liquid and sending it through a series of distillation columns.

31. The process of claim 29, further comprising the step of separating condensed water from the unreacted liquid paraffins and separating condensed water from the light olefins.

* * * * *